United States Patent [19]

Kennington et al.

[11] Patent Number: 5,183,764
[45] Date of Patent: Feb. 2, 1993

[54] QUANTITATIVE ANALYSIS FOR DIABETIC CONDITION PREDICTOR INVOLVING CHIRO-INOSITOL

[75] Inventors: Alison S. Kennington, Laurel, Md.; Joseph Larner, Charlottesville, Va.

[73] Assignee: University of Virginia Alumni Patents Foundation, Charlottesville, Va.

[21] Appl. No.: 870,771

[22] Filed: Apr. 21, 1992

Related U.S. Application Data

[63] Continuation of Ser. No. 476,953, Feb. 8, 1990, abandoned, which is a continuation-in-part of Ser. No. 320,485, Mar. 8, 1989, abandoned, which is a continuation of Ser. No. 751,628, Aug. 26, 1991.

[51] Int. Cl.$^5$ .................. G01N 33/00; G01N 33/49; G01N 33/493
[52] U.S. Cl. .................. 436/131; 436/811; 436/822
[58] Field of Search .............. 436/131, 811, 822

[56] References Cited

PUBLICATIONS

Williamson et al.–Chem. Abst., vol. 105 (1986), p. 18407j.
Kennington et al., "Low Urinary Chiro-Inositol Excretion in Non-Insulin-Dependent Diabetes Mellitus", N. Eng. J. Med., Aug. 9, 1990, pp. 373–378, vol. 323.
Romero et al., "Anti-Inositol Antibodies Selectively Block Some of the Actions of Insulin in Intack BC$_3$H1 Cells", Proc. Natl. Acad. Sci. USA., vol. 87, pp. 1476–1480, Feb. 1990.

*Primary Examiner*—Sam Rosen
*Attorney, Agent, or Firm*—Oblon, Spivak, McClelland, Maier & Neustadt

[57] ABSTRACT

An enhanced quantitative assay for chiro-inositol concentration can be used to determine insulin-resistance, or a predeposition to the development of insulin-resistance, in type I and type II diabetics. Spot urine or serum samples reflecting concentrations of chiro-inositol below about 1.0 micrograms/ml in urine or 0.1 micrograms/ml in serum are indicative of a predisposition to the development of insulin-resistance, while concentrations below about 0.3 micrograms/ml or 0.03 micrograms/ml in serum are associated with actual insulin-resistance symptoms. The assay can be employed for patient diagnosis, insulin therapy monitoring, and family screening.

3 Claims, No Drawings

5,183,764

QUANTITATIVE ANALYSIS FOR DIABETIC CONDITION PREDICTOR INVOLVING CHIRO-INOSITOL

This application is a continuation of application Ser. No. 07/476,953, filed on Feb. 8, 1990, now abandoned; which is a CONT-IN-PART of 07/320,485, filed on Mar. 8, 1989, abandoned for Continuation of 07/751,628 of Aug. 26, 1991, pending.

BACKGROUND OF THE INVENTION

1. Field of the Invention

This invention pertains to a quantitative assay for a marker or predictor of insulin resistance and the associated diabetic condition in mammals, specifically, a quantitative assay which provides for quick screening of individual patients for an indicator of the diabetic state, the absence of chiro-inositol. The assay provides a low-cost, quick method for conducing a preliminary assay for diabetes, or a predilection to the development of diabetes, in mammals, including humans.

2. Background of the Prior Art

As reported in parent application Ser. No. 320,485, discoveries concerning the structures of insulin mediators in mammals, and the presence, in at least one of those mediators, of D-chiro-inositol, led, in part, to the determination that this particular sugar alcohol was absent, or substantially absent, in diabetic individuals, particularly insulin-resistant diabetics, who traditionally are difficult to both identify, and treat.

Further research into this phenomenon led to the determination that both D-chiro-inositol and L-chiro-inositol concentrations in diabetic individuals, particularly type II diabetics, are significantly reduced, and that a quantitative assay for the presence of these "markers" can result in the identification (a) of type II diabetics and (b) individuals at risk or predicted to develop the symptoms of type II diabetes.

U.S. application Ser. No. 320,485, as originally filed, discloses one type of sample to be screened for the presence of D-chiro-inositol. This includes the collection of a 24-hour urine sample, accompanied by convenience of frozen storage, if necessary. Although highly desirable, due to its non-invasive nature, low cost, reliability and speed, further improvements on this process could be obtained.

Accordingly, it remains an object of those of ordinary skill in the art to provide a sensitive, quantitative assay for both D-and L-chiro-inositol, as a marker, indicator or predictor of insulin-reistance and type II diabetes.

SUMMARY OF THE INVENTION

The above objects, and others more fully developed below, are achieved by a quantitative assay for chiro-inositol taken from spot samples of either mammalian urine or serum. Concentrations of chiro-inositol, relative to both normal individuals, and other inositols, appear constant in both types of samples, eliminating the need for a 24-hour urine specimen collection, and providing alternative fluid sources, both for the convenience of the analyst, and for a check on assay results.

One convenient assay system involves the use of conventional gas chromatography/mass spectrophotometry (GC/MS). Other assay methods are known. Chiro-inositol concentrations of 1 micrograms/ml and above in either urine or serum samples is indicative of the normal or control concentrations for chiro-inositols in healthy individuals. A value of 0.3 micrograms - 1 micrograms per ml is suggestive of a mammalian individual at risk for the development of type II diabetes, or may be further indicative of a presymptomatic type II diabetic. Chiro-inositol values below 0.3 micrograms/ml are indicative of type II diabetics. Chiro-inositol concentrations in serum samples are about 10 fold lower than urine. Thus, values in serum of below 0.1 micrograms/ml are indicative of individuals at risk, and values below about 0.03 are indicative of type II diabetes.

It has further been discovered that similar low inositol concentrations can be correlated with type I diabetics demonstrating insulin-resistance, a characteristic of type II diabetics. Thus, sampling of mammalian populations according to the quantitative assay of this invention appears to be indicative of insulin- resistance, exhibited by a limited number of type I diabetics and type II diabetics. Accordingly, the assay may be used both as a confirmatory assay for the presence of type II diabetes in all populations, a confirmation for insulin-resistance in type I diabetics not responding to insulin therapy, as well as a useful tool for family studies and genetic prediction for insulin- resistant individuals, or individuals drawn from families exhibiting insulin-resistance, for generational planning.

DETAILED DESCRIPTION OF THE INVENTION

In the performance of the assay of this invention, a urine or serum sample must be obtained. These samples may be spot samples, and no specific time of day or fasting period is required in order to perform the assay with accuracy and precision. Additionally, concentrations of chiro-inositol in patients exhibiting below normal concentrations appear to be independent of various sugar-lowering agents, including insulin and related agents. If a urine sample is obtained, the sample may be adsorbed onto a conventional anion/cation exchange resin bed, eluted with distilled deionized water, and further purified, through solid phase extraction. The sample collection is recovered in distilled water, dried and derivatized. An exemplary derivatization material is heptafluorobutyrlimidazole. In an alternative embodiment of the invention, a serum sample may be collected and subjected, e.g., to ultrafiltration and then applied to purification resins, and subsequently derivatized, as with the urine specimen discussed above.

Conventionally, the samples prepared may be easily assayed on a gas chromatography/mass spectrometer (e.g. HP5710A chromatograph combined with a JMS D-300JEOL spectrometer).

Spot samples exhibiting chiro-inositol concentration (D- and L- combined) of about 1 micrograms/ml and above are representative of normal concentrations, exhibited by non-diabetic, non-insulin-resistant individuals. Assays reflecting values below about 0.3 micrograms/ml are insulin-resistant. Type I diabetics exhibiting these substantially absent chiro-inositol concentrations should be considered insulin-resistant, when determining proper therapy. The remaining individuals are expected to be type II diabetics.

Values obtained through the assay of this invention of 0.3 micrograms - 1 micrograms/ml are indicative of individuals at risk of development of type II diabetes, or individuals who are presymptomatic type II diabetics. All such readings should be confirmed, of course, by subsequent more involved assays available to those of skill in the art.

Studies on Pima indian populations of Arizona, as well as a patient population in and about the University of Virginia, Charlottesville, Va., and diabetic rhesus monkeys, University of Maryland Primate Center, exhibit a virtual absence of chiro-inositol in diabetic individuals. The marked correlation between chiro-inositol concentrations and insulin-resistance, through these blind-blind studies, was particularly dramatic when compared with the concentrations of structurally related myo-inositol concentrations, which are generally elevated in diabetic patients, and were significantly higher in the diabetic subjects studied than non-diabetics.

Muscle biopsy experiments confirm the findings of low or nonexistent concentrations of chiro-inositol in the patients studied exhibiting non-insulin dependent diabetes mellitus (NIDDM). Given the apparent presence of chiro-inositol in insulin mediators and the correlation between the absence of chiro-inositol and insulin-resistance, applicants believe that there may be a biosynthesis pathway lacking in individuals exhibiting NIDDM and related insulin-resistance or insulin insensitivity, which prevents or retards the formation of a mediator essential in some insulin-activated metabolic pathways. Applicants do not wish to be bound by this theory.

The importance of chiro-inositol as a compound linked to insulin-resistance, and thus linked to individuals requiring non-insulin therapy in the treatment of diabetes, provides a convenient method of monitoring the efficacy of chemical therapy prescribed for the diabetic patient. Those diabetics under some type of chemical therapy, including insulin administration, can be monitored routinely through the assay of this invention for chiro-inositol concentrations. A pronounced drop in the chiro-inositol concentrations, or absence of chiro-inositol from the serum, urine or other sample, is suggestive of insulin-resistance. Additionally, if the individual is on an inositol supplement, in order to treat the deficiency, assays of samples taken some hours subsequent to ingestion of the medication should give an accurate reflection of the value of the treatment.

It should be noted that this invention can be practiced through assays other than GC/MS. A wide variety of assays are known to those of ordinary skill in the art for the detection of specific compounds, and the use of any one which is consistent with a derivatized, dried or liquid sample is appropriate herein. Thus, enzyme reduction/oxidation potential measurements, using, e.g., an immobilized enzyme specific for chiro-inositol, the immobilized enzyme being in a fixed relationship to an electrode, may be used. The presence of chiro-inositol will result in the enzyme-catalyzed reaction going forward, altering the electrical environment detected by the electrode. Alternative assay that can be employed may include antibody assays, e.g., ELISA, LISA, agglutination assays and the like. All such assays are within the context of the invention claimed herein.

The above invention has been described with reference to specific examples and materials. It should be clear that these specifics can be varied without departing from the scope of the invention. In particular, alternative resins in the purification format, alternation of the purification sequence, and alternative assay forms, sensitive to chiro-inositol may be employed, without departing from the scope of the invention, as defined by the claims appended hereto.

What is claimed is:

1. A method for screening mammalian individuals to determine whether the individual exhibits insulin-resistance associated with a diabetic state, comprising:
   obtaining a sample from said individual, said sample being selected from the group consisting of a serum sample, and a urine sample,
   determing the concentration of chiro-inositol (CI) in said sample,
   correlating said concentration with preestablished values indicating insulin-resistance in mammalian individuals,
   wherein said preestablished values are less than about 0.3 micrograms/ml for urinary CI concentrations and less than about 0.03 micrograms/ml for serum CI concentrations being indicative of insulin-resistance.

2. A method for screening mammalian individuals to determine whether said individuals exhibit presymptomatic insulin-resistance, comprising:
   obtaining a sample from said individual, said sample being selected from the group consisting of a serum sample and a urine sample,
   determining the concentration of chiro-inositol (CI) in said individual,
   correlated said CI concentration with preestablished values indicting presymptomatic insulin-resistance in mammalian individuals,
   wherein said preestablished values are between about 0.3–1.0 micrograms/ml for urinary CI concentrations and between about 0.03–0.1 micrograms/ml for CI serum concentrations being indicative of presymptomatic insulin-resistance in mammalian individuals.

3. A method for screening mammalian individuals to determine whether said individuals exhibit insulin-resistance, comprising:
   obtaining a sample from said individual, said sample being selected from the group consisting of a serum sample and a urine sample,
   determining the concentration of chiro-inositol in said individual,
   correlating said chiro-inositol concentration with preestablished values indicating insulin-resistance in mammalian individuals,
   wherein said preestablished values are between about 0.3–1.0 micrograms/ml for urinary chiro-inositol concentrations and between about 0.03–0.1 micrograms/ml for chiro-inositol serum concentrations being indicative of insulin-resistance in mammalian individuals.

* * * * *